United States Patent [19]

Crupi, Jr.

[11] Patent Number: 5,103,811
[45] Date of Patent: Apr. 14, 1992

[54] BODY PART OR JOINT BRACE

[76] Inventor: Theodore P. Crupi, Jr., 591 Edgegrove Ave., Staten Island, N.Y. 10312

[21] Appl. No.: 550,073

[22] Filed: Jul. 9, 1990

[51] Int. Cl.$^5$ ............................ A61F 5/00; A61F 2/74
[52] U.S. Cl. .................................... 602/16; 623/26; 602/23; 602/26
[58] Field of Search ................. 128/77, 80 R, 80 F, 128/80 C, 87 R, 88, 75, 78, 84 R, 84 C; 623/26, 28

[56] References Cited

U.S. PATENT DOCUMENTS

| | | | |
|---|---|---|---|
| 1,589,670 | 6/1926 | Vartia | 128/78 |
| 2,568,052 | 9/1951 | Catranis | 623/26 |
| 2,671,224 | 3/1954 | Regnell | 623/26 |
| 3,316,558 | 5/1967 | Mortensen | 623/26 |
| 3,631,542 | 1/1972 | Potter | 128/77 |
| 3,799,159 | 3/1974 | Scott | 128/80 C |
| 4,508,111 | 4/1985 | Hepburn | 128/88 |
| 4,958,705 | 9/1990 | Horvath | 623/26 |

FOREIGN PATENT DOCUMENTS 0585843 12/1977 U.S.S.R. ................... 128/78
1183097 10/1985 U.S.S.R. ................... 128/87 R

Primary Examiner—Richard J. Apley
Assistant Examiner—Karen G. Horowitz
Attorney, Agent, or Firm—Kenyon & Kenyon

[57] ABSTRACT

A bracket for a body part comprising a first member attachable to a first portion of the body part, a second member attachable to a second portion of the body part, the first and second members being spaced apart a predetermined distance, a force applying device disposed between the first and second members and coupled to the members for exerting a force between the members, a control device in communication with the force applying device for activating the force applying device to generate a force between the first and second members, and a flexible coupling for coupling the force applying device to at least one of the first and second members to allow flexing of the body part, the force applying device providing a force between the first and second members and thus across the body part when the body part is in an unflexed, straight position.

9 Claims, 5 Drawing Sheets

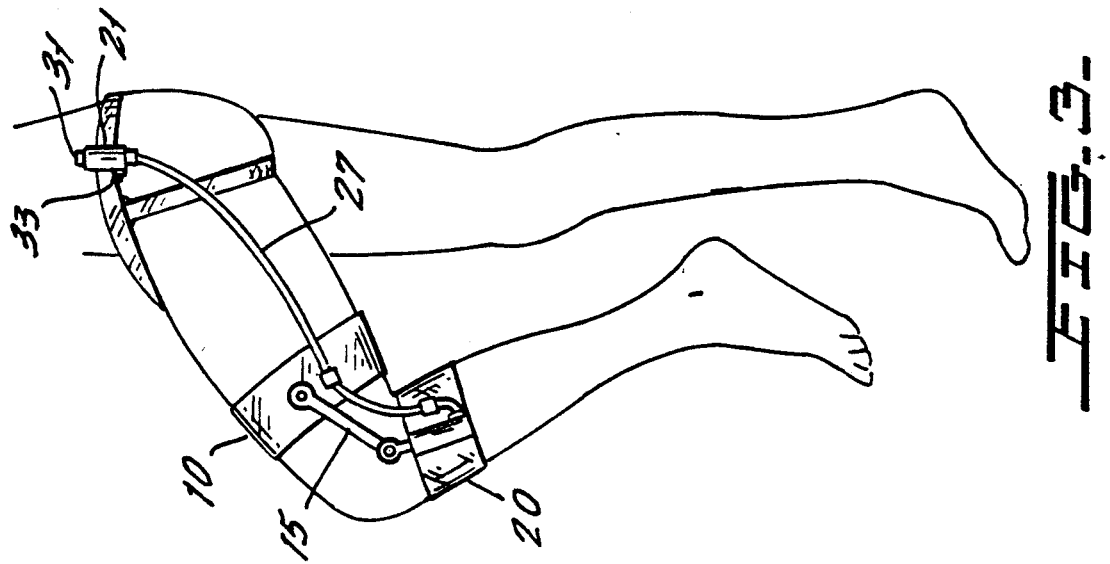
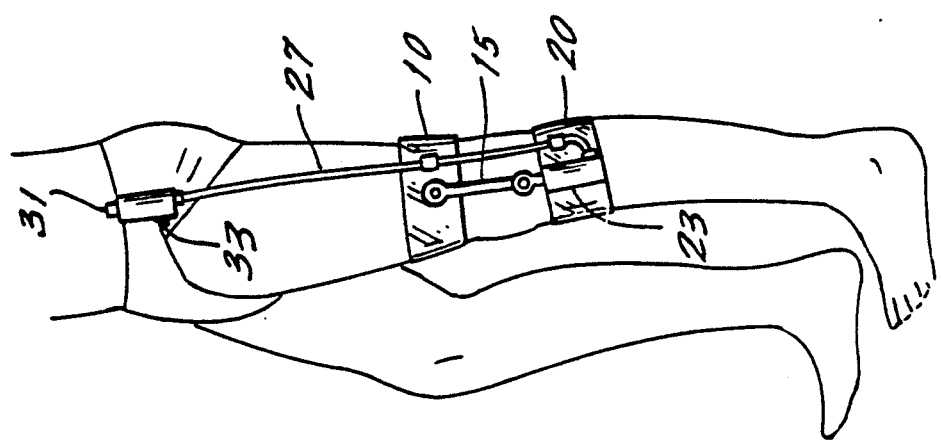
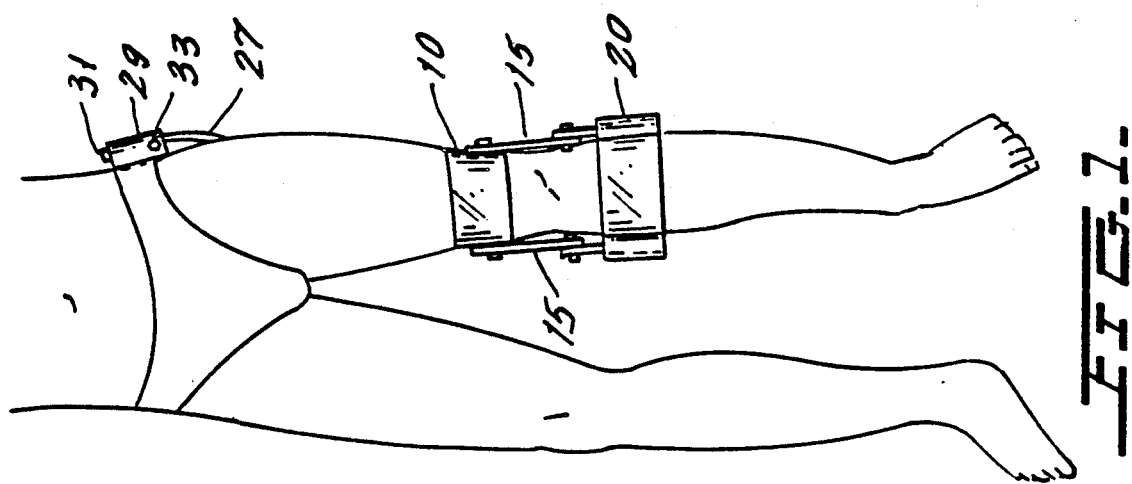

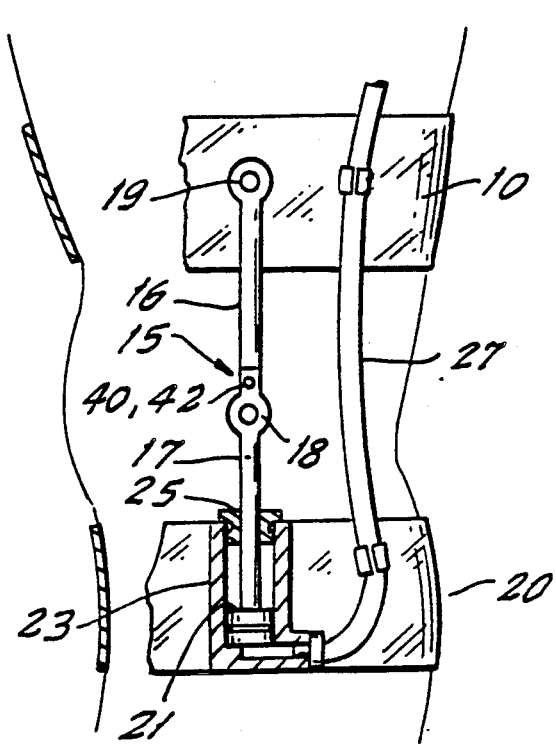
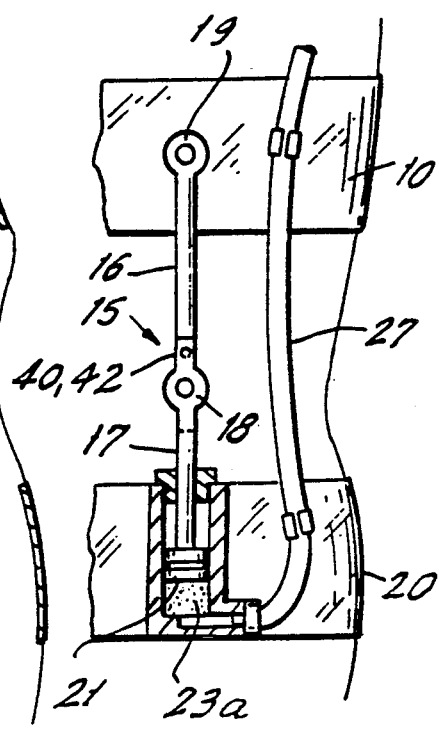
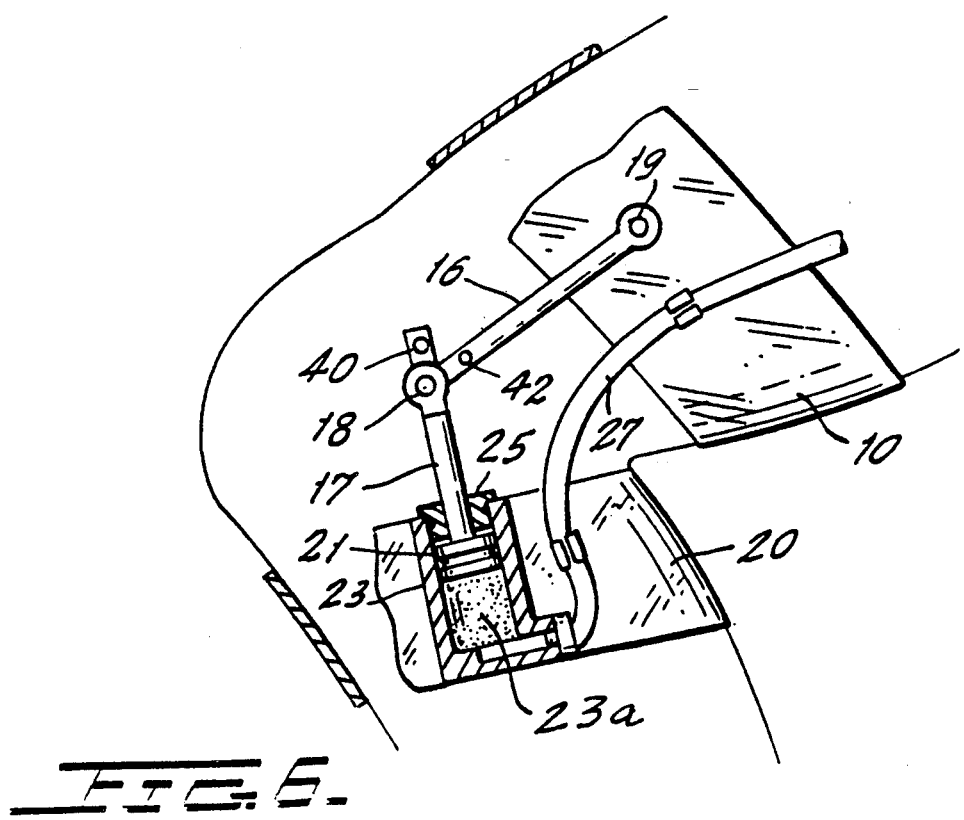

BODY PART OR JOINT BRACE

BACKGROUND OF THE INVENTION

The present invention relates to a brace for anatomical joints and body parts, and in particular, to a brace which provides a degree of traction or separating force to the body part or joint, e.g., a human bone joint, to relieve pressure on the joint, but yet which at the same time allows the joint to flex freely. In particular, the present invention allows pressure due to weight to be removed from a joint or body part, but at the same time allows the joint or body part to be freely moved, for example, if used with a knee joint, the device allows the user to walk and to continue to flex the joint but yet removes weight from the joint when the user's weight bears down on the joint.

U.S. Pat. No. 3,799,159 to Scott discloses an hydraulic flexion control device in which a spring is provided between an upper and a lower portion of a brace, with a cable provided through the spring operated by an hydraulic device such that when the cable is loosened by the hydraulic device, flexion is allowed, i.e., the spring can bend. When the hydraulic device is activated, the cable is drawn taut, preventing the spring from bending and locking the joint rigidly.

Other patents for various other types of stretching and traction devices are known, for example, U.S. Pat. Nos. 1,589,670, 3,889,664, 3,915,161, 3,827,429, 3,799,156, 3,028,858, 3,878,842, 4,245,627 and 4,715,363 allow pressure to be relieved or traction to be applied to various parts of the human body.

SUMMARY OF THE INVENTION

It is an object of the present invention to provide a novel form of joint or body part brace, which can be applied to various parts of the human body.

It is a further object of the present invention to provide such a joint or body part brace which allows traction to be exerted on a human joint, and in particular, which allows traction or tension to be provided to a joint or body part when pressure is applied to the joint or part, for example, during walking, yet which at the same time allows the joint or part to be freely flexed.

It is yet still a further object of the present invention to provide such a joint or body part brace which utilizes various force applying means in order to provide the required traction when necessary and which is controllable to remove the traction when desired by the user.

The above and other objects are achieved by a brace for a body part comprising a first member attachable to a first portion of the body part, a second member attachable to a second portion of the body part, the first and second members being spaced apart a predetermined distance, force applying means disposed between the first and second members and coupled to the members for exerting a force between the members, control means in communication with the force applying means for activating the force supplying means to generate a force between the first and second members, and flexible means coupling the force applying means to at least one of the first and second members to allow flexing of the body part, the force applying means providing a force between the first and second members and thus across the body part when the body part is in an unflexed, straight position.

BRIEF DESCRIPTION OF THE DRAWINGS

The invention will be described in greater detail in the following detailed description with reference to the drawings in which:

FIG. 1 shows a front view of the joint or body part brace according to the invention applied to the knee of a human being;

FIG. 2 is a side view of the joint or body part brace showing FIG. 1;

FIG. 3 shows a side view of the joint or body part brace during flexing;

FIG. 4 shows the joint or body part brace in cross section when traction is not being applied to the joint;

FIG. 5 shows the joint or body part brace in cross section in its activated state whereby traction is applied to the joint;

FIG. 6 shows the joint or body part brace during flexing when traction is being applied to the joint;

DETAILED DESCRIPTION

Figure 8:
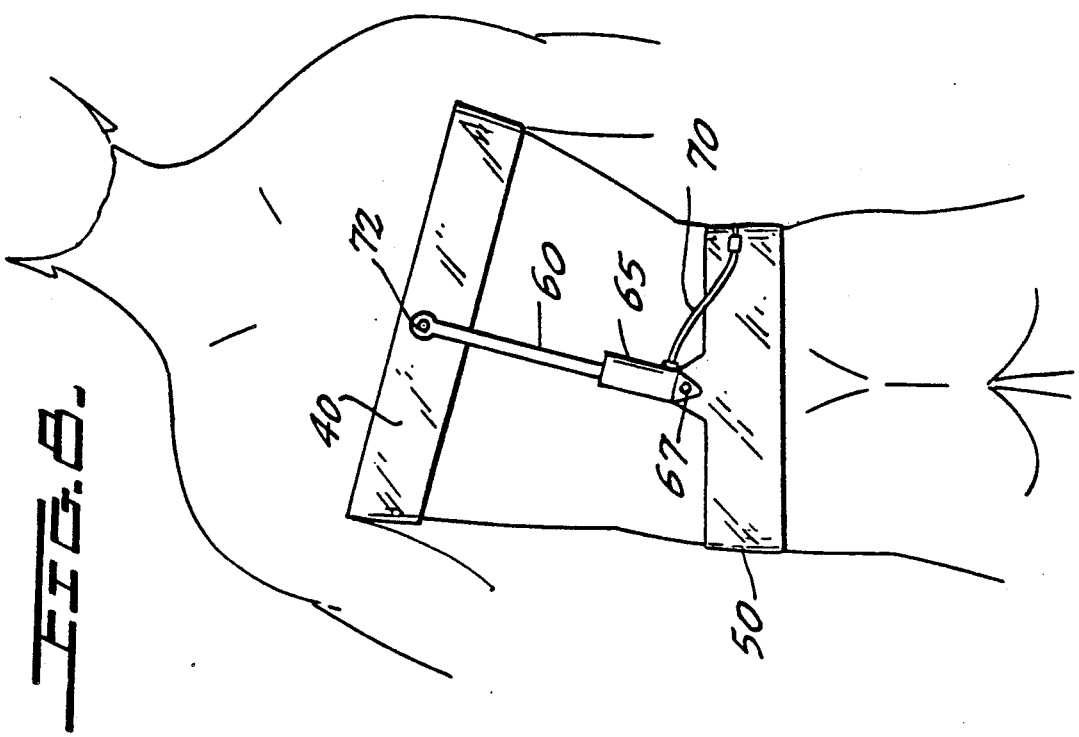
FIG. 8 shows the joint or body part brace according to the present invention applied to the spinal column showing how it allows flexing of the user's body.

With reference now to the drawing figures, the joint or body part brace according to the present invention may be applied to a human body part, for example, a body joint, and may be applied to the knee of a user as shown in FIGS. 1 to 6. The joint or body part brace comprises an upper brace portion and a lower brace portion 20, and preferably comprises two articulated sections 15, preferably disposed alongside the joint. The articulated sections include a first upper portion 16 and a second lower portion 17, coupled together at a pivot point 18. Upper portion 16 may be coupled to the upper brace portion 10 via a rigid or pivotable connection 19. In the illustrated embodiment, lower portion 17 of the articulated member 15 is coupled to a piston 21 disposed in a cylinder 23. Member 17 forms the piston rod for piston 21 and is held in position in cylinder 23 by suitable sealing means or bearing or bushing means 25. The interior of cylinder 23 is in fluid communication with a tubing 27 coupled to a control member and reservoir 29 including a pump button 31 and a check valve 33.

Upper brace portion 10 and lower brace portion 20 are suitably made of materials so that the portion in contact with the body is appropriately cushioned for comfort while the exterior is made suitably rigid so as to be able to support the articulated sections 15.

In operation, when the user desires to provide traction to the joint or body part, the user operates the button 31 by pumping the pump button to provide fluid in the reservoir 29 through the tubing 27 into the cylinder 23 to force the piston upwardly, as shown in FIG. 5, thereby providing tension to the joint, in this case the knee joint. Check valve 33 is provided so that fluid once pumped into the cylinder 23, as shown by the fluid contained in the space 23a in FIG. 5, does not flow back into the reservoir 29. If the user desires to relieve the tension provided by the hydraulic fluid, control button 31 is operated, thereby allowing fluid to flow back into the reservoir 29, relieving the tension on the joint.

As shown in FIG. 6, the joint brace of the present invention allows the user to continue to flex the joint. When the user bears down on and straightens the joint, for example, during walking by placing weight on the joint when the user's foot touches the ground, the present invention keeps the two portions of the joint under tension when weight is placed on the joint, one of the objects of the invention. For example, by placing such tension on the joint, pressure is eliminated from the joint thereby reducing pain to an injured joint during walking.

Figure 9:
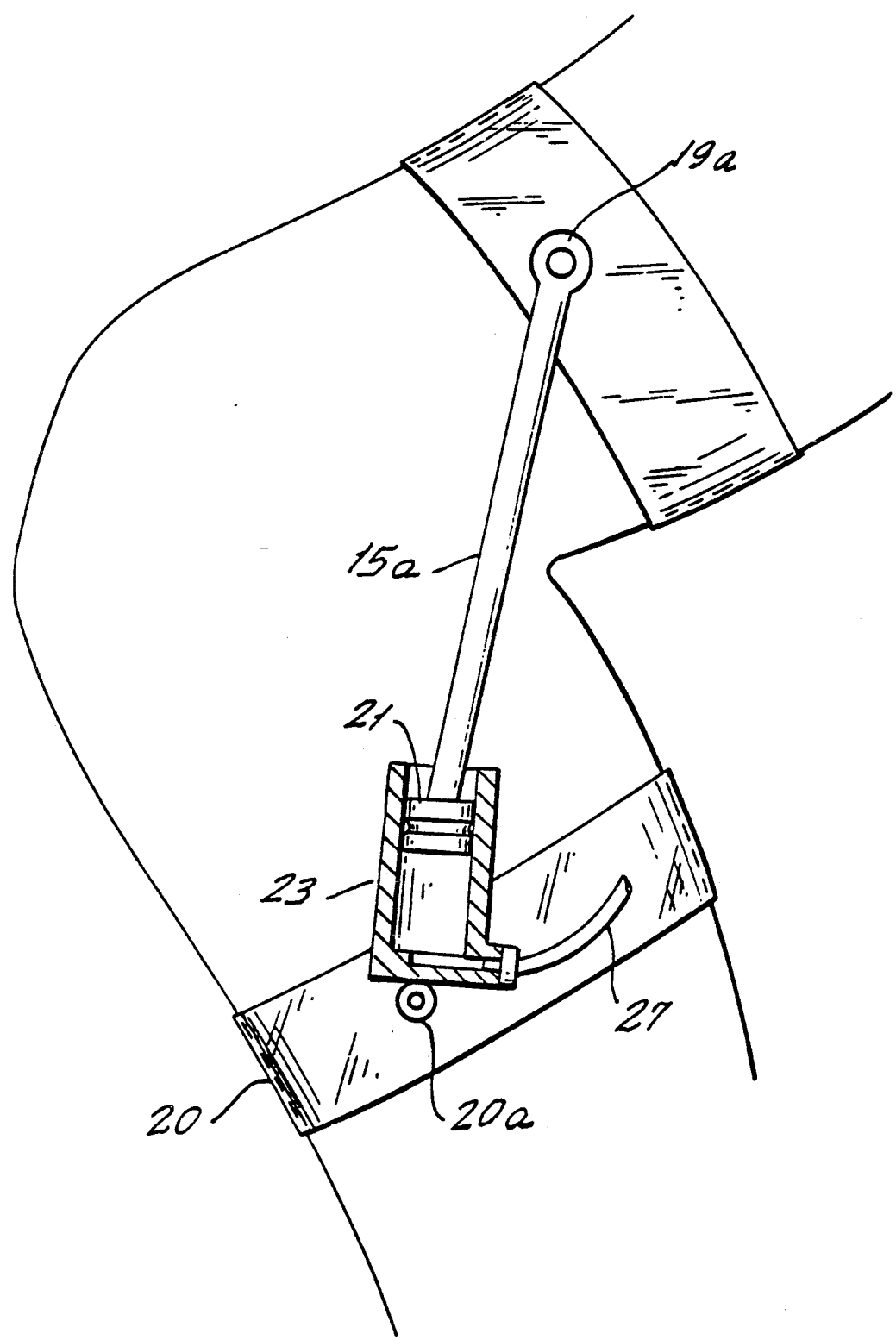
FIG. 9 shows an alternative embodiment of the joint or body part brace according the present invention applied to the knee of a user.

FIG. 9 shows another embodiment of the present invention where an articulated member 15 of the embodiment shown in FIGS. 1 through 6 is replaced by a single rod 15a having a pivoted mounting 19a to upper brace portion 10 and wherein the cylinder 23 is pivotably mounted at 20a to lower brace portion 20, thus allowing flexing of the joint much as in the embodiment shown in FIGS. 1 through 6, but allowing tension to be applied to the joint as necessary through the piston 21 in the hydraulic cylinder 23.

Figure 7:
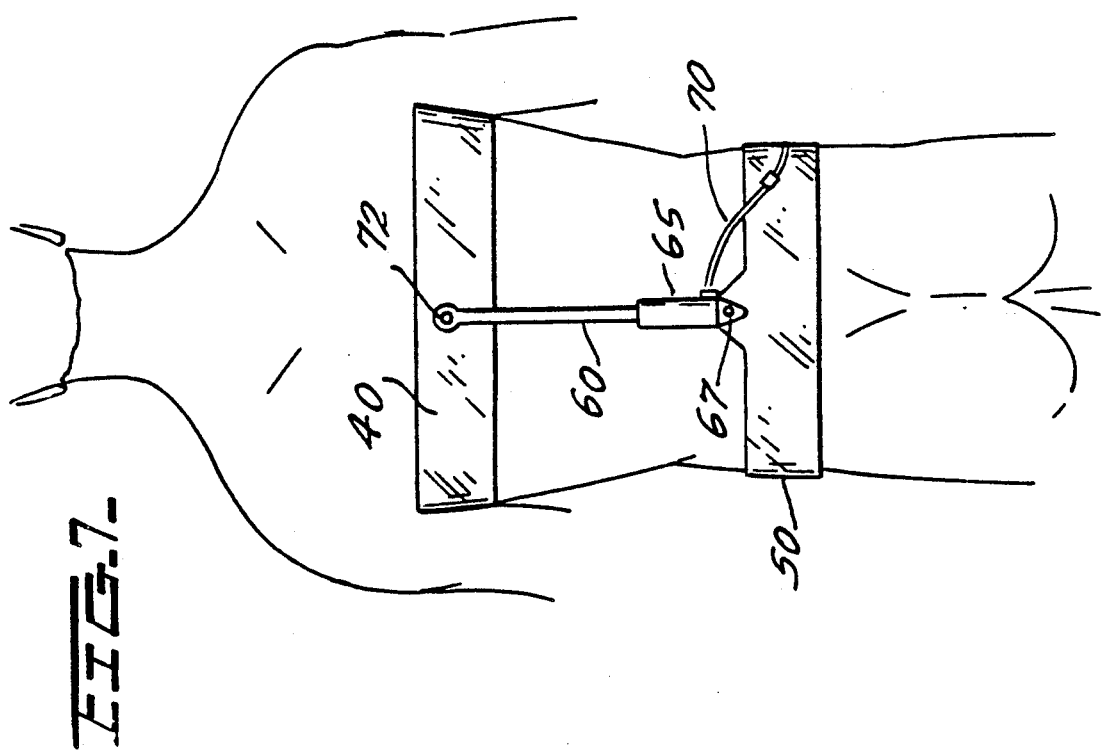
FIG. 7 shows the joint or body part brace according to the present invention being applied to the spinal column of the user to provide traction.

FIGS. 7 and 8 show the device according to the present invention applied to a back brace. As shown in FIGS. 7 and 8, an upper portion 40 of the brace and a lower portion 50 of the brace are provided, with a rod 60 coupled between the upper brace portion 40 and the lower brace portion 50. The rod 60 is connected to a piston contained with an hydraulic piston-cylinder arrangement 65 which is pivotally coupled to the lower portion 50 at 67. A suitable hydraulic line 70 is provided coupled to a control device, not shown, which is similar to the reservoir control device 29 shown in FIGS. 1 to 3. Rod 60 may be coupled to upper brace portion 40 at 72 pivotably or by a rigid connection.

As shown in FIG. 8, the device according to the present invention allows tension or traction to be applied to the human body, in this case the spine, by suitable control of the hydraulic device 65. At the same time it allows flexing of the body part to which it is attached.

Although the present invention has been described with reference to an hydraulic piston-cylinder arrangement, other means for applying force may be used. For example, instead of an hydraulic fluid, compressed air could be used in which case the user would be provided with a small air pump in the control device 29 which would obtain air from the atmosphere in order to displace piston 21 in its cylinder 23. Other means could also be employed, for example, suitably activated springs or electrically controlled devices such as, for example, solenoids coupled to suitable mechanical arrangements, e.g., rods, for providing the necessary tension to the human body part.

The brace according to the present invention can also be used automatically such that the fluid pressure in the interior of cylinder 23 is increased only when the joint is straightened and unflexed. Thus, for example, piston 21 can be driven upwardly only when the joint is straightened and pressure is thus applied only at that time, with the pressure being relieved when the joint is flexed. Suitable sensor means can be employed for determining when the joint is straightened.

In a further embodiment, a locking device can be employed to lock the joint rigidly when the joint is in the unflexed straightened position, thereby providing traction to the joint at all times and preventing the joint from flexing. Such a locking device might comprise, e.g., a thumbscrew 40 cooperating with a detent 42 in one of the rod portions 16 or 17, as shown in FIGS. 4 and 6.

Figure 10:
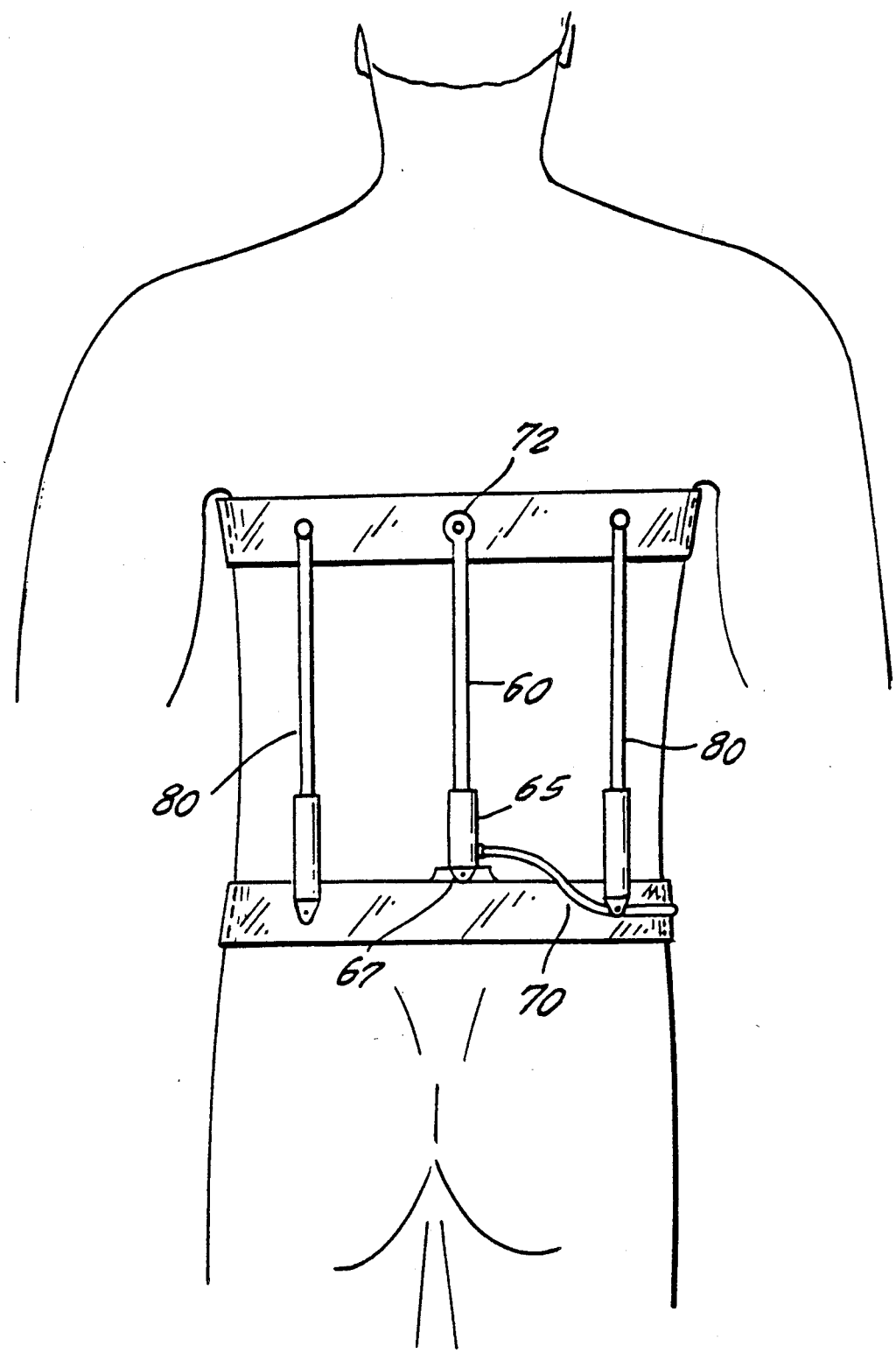
FIG. 10 shows a further embodiment of the brace of FIGS. 7 and 8.

Additionally, in order to provide additional stability or to restrict movement in a particular direction, additional mechanical arrangements or additional force supplying devices could be provided. For example, in FIGS. 7 and 8, additional rods could be provided alongside the piston cylinder 65 to lock the body part from sideways flexing, i.e., to prevent movement sideways as shown in FIG. 8, allowing pivoting movement only from front to back. With such an arrangement, the user could lock a telescoping rod, for instance, into fixed position to prevent or restrict side-to-side movement. This could be done with a suitable remotely actuated mechanism or by direct actuation. Alternatively, additional piston-cylinder assemblies could be provided to generate the necessary locking forces. An example is shown in FIG. 10. In FIG. 10, two additional piston cylinders or telescoping rods 80 are provided to restrict or prevent sideways or left-to-right movement while allowing front-to-back pivoting It is also conceivable that the piston-cylinders or other force applying devices of the present invention could be controlled automatically or at a user's discretion to provide joint or body part exercise or to control movement, e.g., walking or moving an arm.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are, accordingly, to be regarded in an illustrative rather than in a restrictive sense.

What is claimed is:

1. A brace for a body part comprising:
a first member encircling a first portion of the body part;
a second member encircling a second portion of the body part, said first and second members being spaced apart a predetermined distance;
force applying means disposed between the first and second members and coupled to said members for exerting a force between said members to provide tension to the joint or body part disposed between said first and second portions of the body part;
control means in communication with said force applying means for activating said force applying means to generate a force between said first and second members; and
flexible means coupling said force applying means to at least one of said first and second members to allow flexing of the body part, said force applying means providing a force between said first and second members and thus across said body part when said body part is in an unflexed, straight position and also when in a flexed, bent position, said flexible means comprising a pivotally mounted rod coupling said force applying means to one of said first and second members, said control means being disposed remotely from said force applying means, with a communication link being disposed between said control means and said force applying means, said control means being disposed such that it may be mounted remotely from the force applying means at a point on a wearer's body such that it is convenient for manual operation, whereby tension or traction may be applied to said body part while at the same time flexing of said body part is allowed.

2. The brace recited in claim 1, wherein said force applying means comprises a hydraulic piston and cylinder.

3. The brace recited in claim 2, wherein said control means comprises an hydraulic pump means in fluid communication with said hydraulic piston and cylinder.

4. The brace recited in claim 3, wherein said control means is coupled to said hydraulic piston and cylinder by a fluid line.

5. The brace recited in claim 4, wherein said control means further includes a check valve disposed in said fluid line.

6. The brace recited in claim 1, wherein said force applying means is coupled directly to the other of said first and second members.

7. The brace recited in claim 6, wherein said rod comprises first and second rods coupled together, said first rod coupled to one of said first and second members, said first rod having a pivot point coupled to the second rod, the second rod being coupled to said force applying means.

8. The brace recited in claim 6, wherein said force applying means is coupled directly to one of said first and second members by a pivotable joint member, and said rod is connected to the other of said first and second members by a further pivotable joint disposed on said latter member.

9. The brace recited in claim 1, further comprising additional force supplying means for restricting movement of the body part in at least one direction.

* * * * *